(12) United States Patent
Herold et al.

(10) Patent No.: US 7,153,675 B2
(45) Date of Patent: Dec. 26, 2006

(54) PROCESS FOR THE PREPARATION OF SUBSTITUTED CARBOXYLIC ESTERS

(75) Inventors: Peter Herold, Basel (CH); Stefan Stutz, Basel (CH)

(73) Assignee: Speedel Pharma AG, Basel (CH)

( * ) Notice: Subject to any disclaimer, the term of this patent is extended or adjusted under 35 U.S.C. 154(b) by 345 days.

(21) Appl. No.: 10/477,739

(22) PCT Filed: Apr. 26, 2002

(86) PCT No.: PCT/EP02/04640

§ 371 (c)(1),
(2), (4) Date: Nov. 14, 2003

(87) PCT Pub. No.: WO02/092828

PCT Pub. Date: Nov. 21, 2002

(65) Prior Publication Data

US 2004/0132148 A1 Jul. 8, 2004

(30) Foreign Application Priority Data

May 15, 2001 (CH) .................................... 0895/01

(51) Int. Cl.
- *C12P 7/62* (2006.01)
- *C12P 7/40* (2006.01)
- *C07C 69/02* (2006.01)

(52) U.S. Cl. ...................... 435/135; 435/136; 560/129

(58) Field of Classification Search ................ 435/135, 435/136; 560/129

See application file for complete search history.

(56) References Cited

U.S. PATENT DOCUMENTS 6,406,912 B1 * 6/2002 Holla .......................... 435/122
6,777,574 B1 * 8/2004 Herold et al. ............... 560/129

FOREIGN PATENT DOCUMENTS

| WO | 96 40975 | 12/1996 |
| WO | 99 45133 | 9/1999 |
| WO | 01 09083 | 2/2001 |

* cited by examiner

*Primary Examiner*—James O. Wilson
*Assistant Examiner*—Ebenezer Sackey
(74) *Attorney, Agent, or Firm*—Wenderoth, Lind & Ponack, L.L.P.

(57) ABSTRACT

A process for the preparation of 2(S)-alkyl-5-halogenpent-4-ene carboxylic esters by enzymatic hydrolysis, comprising the steps: a) enzymatic hydrolysis of racemic 2-alkyl-5-halogenpent-4-ene carboxylic esters in aqueous and alkaline medium in the presence of an esterase; b) isolation of 2(S)alkyl-5-halogenpent-4-ene carboxylic esters by extraction with an organic solvent; c) isolation of 2(R)-alkyl-5-halogenpent-4-ene carboxylic acids from the aqueous-alkaline medium; d) Esterification of 2(R)-alkyl-5-halogenpent-4-ene carboxylic acids, e) subsequent racemization to form 2-alkyl-5-halogenpent-4-ene carboxylic esters; and f) return of the racemate obtained in step e) to step a), if necessary together with fresh racemic 2-alkyl-5-halogenpent-4-ene carboxylic esters. The process permits the undesired R-stereoisomers to be converted into the desired 2(S)-alkyl-5-halogenpent-4-ene carboxylic esters to avoid waste product from the synthesis.

23 Claims, No Drawings

PROCESS FOR THE PREPARATION OF SUBSTITUTED CARBOXYLIC ESTERS

The invention relates to the preparation of 2(S)-alkyl-5-halogenpent-4-ene carboxylic esters, in which the 2(S)-stereoisomer is obtained by enzymatic hydrolysis of the racemate, followed by esterification then racemization of the resulting 2(R)-alkyl-5-halogenpent-4-ene carboxylic acid, and returning the resulting racemic 2-alkyl-5-halogenpent-4-ene carboxylic ester to the process.

In EP-A-0 678 503, δ-amino-γ-hydroxy-ω-aryl-alkanecarboxamides are described, which exhibit renin-inhibiting properties and could be used as antihypertensive agents in pharmaceutical preparations.

In WO 01/09079, a multistep manufacturing process is described, in which the central intermediate is a 2,7-dialkyl-8-aryl-4-octenoylamide of formula A

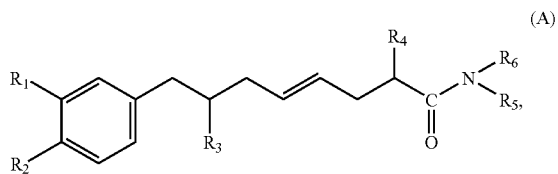

(A)

and in particular of formula A1,

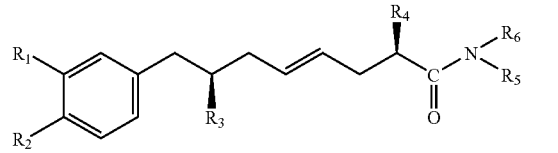

(A1)

wherein $R_1$ and $R_2$ independently of one another are H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is $C_1$–$C_6$alkyl, $R_5$ is $C_1$–$C_6$alkyl or $C_1$–$C_6$alkoxy, or $R_5$ and $R_6$ together are tetramethylene, pentamethylene, 3-oxa-1,5-pentylene or —$CH_2CH_2O$—C(O)— substituted if necessary with $C_1$–$C_4$alkyl, phenyl or benzyl.

The compounds of formulae A and A1 are obtainable by reacting a compound of formula B

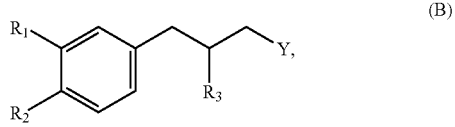

(B)

as racemate or enantiomer, with a compound of formula C, as racemate or enantiomer,

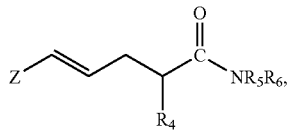

(C)

wherein $R_1$ to $R_4$, $R_5$ and $R_6$ are as defined above, Y is Cl, Br or I and Z is Cl, Br or I, in the presence of an alkali metal or alkaline earth metal. Y and Z are preferably Br and especially Cl.

In WO 01/09083, the compounds of formula C as racemates and 2(S)-stereoisomers are described as well as their preparation. The stereoisomers are obtained by hydrolysis of corresponding racemic carboxylic esters to form their carboxylic acids, followed by racemate separation by means of salt formation with chiral amine bases and crystallization. A stereoselective synthesis is further described for the preparation of 2(S)-pentene carboxylic acids and their derivatization to form the corresponding pentene carboxylic acid halides, esters and amides. This stereoselective synthesis of the esters is not yet satisfactory and is regarded as too costly.

The racemic compounds of formula D

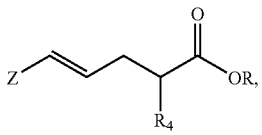

(D)

are prepared as described in WO 01/09083 by coupling of 3-alkylbutane carboxylic esters with trans-1-halogenmethyl-2-halogenethylene. Isolation of the 2(S)-alkyl-5-halogenpent-4-ene carboxylic ester is not described, but only the possibility is disclosed of performing a racemate resolution of the carboxylic esters obtained in the synthesis by means of esterases, in which the very stable 2(R)-alkyl-5-halogenpent-4-ene carboxylic acid is then formed as a by-product. It is extremely desirable to convert the entire racemate directly into the 2(S)-carboxylic ester of formula D, especially since these carboxylic esters may be used in a new stereoselective synthesis for the preparation of a central intermediate of formula A2

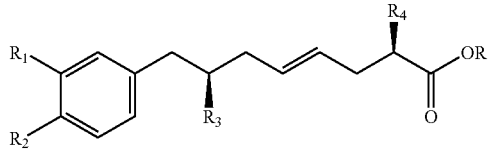

(A2)

directly instead of the compound of formula C according to the above coupling reaction. These carboxylic esters may of course also be converted to the 2(S)-carboxylic amides of formula C for use in the above coupling reaction.

However, a fundamental disadvantage of racemate resolution remains. Not more than 50% of the desired stereoisomer is obtainable. The 2(R)-stereoisomer must be disposed of together with processing losses arising from the racemate resolution. These large quantities make racemate resolution completely uneconomical. A more effective method is therefore needed in which, above all, the occurrence of these large waste disposal quantities is reduced or prevented.

It has now been surprisingly found that, in the preparation of 2(S)-alkyl-5-halogenpent-4-ene carboxylic esters, the occurrence of large quantities of waste products can be avoided and even that only very minor losses have to be expected using enzymatic racemate resolution, if the 2(R)-alkyl-5-halogenpent-4-ene carboxylic acid formed by enzymatic hydrolysis is isolated and returned to the separation process. The recycling ensures overall an extremely economical process, since the total yields are high and only unavoidable processing losses have to be expected. The recycling also offers outstanding ecological advantages, because the formation of waste products overall is reduced to a minimum, and a costly disposal of large quantities of synthesis products can be avoided.

The object of the invention is a process for the preparation of 2(S)-alkyl-5-halogenpent-4-ene carboxylic esters by enzymatic hydrolysis, comprising the steps a) enzymatic hydrolysis of racemic 2-alkyl-5-halogenpent-4-ene carboxylic esters in aqueous and alkaline medium in the presence of an esterase;
b) isolation of 2(S)-alkyl-5-halogenpent-4-ene carboxylic esters by extraction with an organic solvent;
c) isolation of 2(R)-alkyl-5-halogenpent-4-ene carboxylic acids from the aqueous-alkaline medium;
d) Esterification of 2(R)-alkyl-5-halogenpent-4-ene carboxylic acids,
e) subsequent racemization to form 2-alkyl-5-halogenpent-4-ene carboxylic esters; and
f) return of the racemate obtained in step e) to step a), if necessary together with fresh racemic 2-alkyl-5-halogenpent-4-ene carboxylic esters.

The 2(S)-alkyl-5-halogenpent-4-ene carboxylic esters may correspond to formula I,

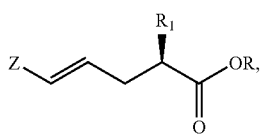

(I)

wherein
$R_1$ is $C_1$–$C_6$alkyl, Z is chlorine, bromine or iodine, and the OR group forms an ester group with the carbonyl residue.
The racemate may correspond to formula II,

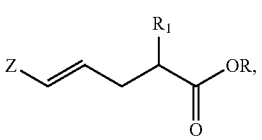

(II)

wherein
$R_1$ is $C_1$–$C_6$alkyl, Z is chlorine, bromine or iodine, and the OR group forms an ester group with the carbonyl residue.
The 2(S)-alkyl-5-halogenpent-4-ene carboxylic acid may correspond to formula III,

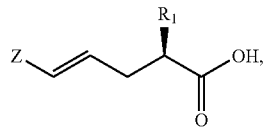

(III)

wherein
$R_1$ is $C_1$–$C_6$alkyl, and Z is chlorine, bromine or iodine.
R1 is preferably $C_1$–$C_4$alkyl. Examples of alkyl are methyl, ethyl, n- and i-propyl, n-, i- and t-butyl, pentyl and hexyl. It is very particularly preferred when $R_4$ is i-propyl.
It is especially preferred when Z is Cl.
In the ester group, R is preferably an organic group with 1 to 18, preferably 1 to 12, and especially preferably 1 to 8 C-atoms and if necessary comprises heteroatoms selected from group O and N.
R may be a branched and preferably linear alkyl, which preferably comprises 1 to 18, especially preferably 1 to 12, and—with particular preference—1 to 6 C atoms. Some examples are methyl, ethyl, n-propyl, n-butyl, pentyl, hexyl, heptyl, octyl, nonyl, decyl, undecyl, dodecyl, teradecyl, hexadecyl and octadecyl. Especially preferred are methyl and ethyl. The alkyl may be substituted, for example with $C_1$–$C_4$alkoxy, such as methoxy or ethoxy. Examples of substituted alkyl are methoxyethyl and ethoxyethyl.
R may be cycloalkyl with 3 to 8, and preferably 5 or 6 ring-carbon atoms. Examples are cyclopropyl, cyclobutyl, cyclohexyl, cyclopentyl, cyclohexyl, cycloheptyl and cyclooctyl. The cycloalkyl may be substituted with $C_1$–$C_4$alkyl or $C_1$–$C_4$alkoxy.
R may be cycloalkyl-$C_1$–$C_4$alkyl with 3 to 8, and preferably 5 or 6 ring-carbon atoms, which is unsubstituted or substituted with $C_1$–$C_4$alkyl or $C_1$–$C_4$alkoxy. Examples are cyclopentylmethyl, cyclohexylmethyl, methylcyclohexylmethyl and cyclohexylethyl.
R may be $C_6$–$C_{10}$aryl which is unsubstituted or substituted with $C_1$–$C_4$alkyl or $C_1$–$C_4$alkoxy. Examples are phenyl, naphthyl, methylphenyl, ethylphenyl and i-propylphenyl.
R may be $C_6$–$C_{10}$aryl-$C_1$–$C_4$alkyl which is unsubstituted or substituted with $C_1$–$C_4$alkyl or $C_1$–$C_4$alkoxy. Examples are benzyl, methylbenzyl and phenylethyl.
Especially preferred compounds of formulae I, II and III are those wherein Z is chlorine, $R_1$ is $C_1$–$C_4$alkyl and especially preferably i-propyl. In compounds of formulae I and II, R is preferably $C_1$–$C_4$alkyl.
A quite especially preferred embodiment comprises compounds of formulae I, II and III wherein Z is chlorine and $R_1$ is i-propyl, as well as compounds of formulae I and II wherein R is methyl or ethyl.
Particularly preferred are compounds of formulae I and II wherein Z is chlorine, $R_1$ is i-propyl, and R is methyl or ethyl.

Process Step a)

The enzymatic hydrolysis of racemic carboxylic esters is known per se and familiar to a person skilled in the art. On hydrolysis, the property of the stereospecific hydrolysis of esterases is exploited to hydrolyse only specific enantiomers by catalytic conversion. These esterases are known and commercially available. The esterases are generally used in catalytic quantities, for example 0.001 to 10 and preferably 0.01 to 5 percent by weight, related to the carboxylic acid. The reaction is carried out in aqueous medium, in which the presence of pH buffers that can keep the pH value constant is favourable. It is expedient to adjust the pH value to slightly alkaline, for example in the range more than 7 to 10, preferably 7.5 to 9. The aqueous medium may contain organic solvents miscible with water, especially alcohols such as methanol, ethanol, n- or i-propanol and butanol. Many buffer agents are known; phosphate buffers are especially suitable. The process may be carried out at slightly elevated reaction temperatures, for example from room temperature to 60° C. It is expedient to conduct the hydrolysis using diluted bases of alkali metals and alkaline earth metals, especially sodium or potassium hydroxide. The consumption of hydroxides can be followed and the endpoint of the reaction thus determined. Aqueous hydroxide solutions may be added altogether or in portions, for example drop by drop.

Process Step b)

To isolate the non-hydrolysed carboxylic esters of formula I, an inert organic solvent or solvent mixture which dissolves the ester and is not miscible with water, and which can therefore be readily separated through the formation of a two-phase system, is added to the reaction mixture. Suitable solvents are hydrocarbons (pentane, hexane, cyclohexane, methyl cyclohexane, benzene, toluene and xylene), halogenated hydrocarbons (methylene chloride, chloroform, tetrachloroethane), ketones (acetone, methyl isobutyl ketone), and ethers (diethyl ether, di-n-propyl ether, dibutyl ether, i-propyl methyl ether, t-butyl methyl ether, ethylene glycol dimethyl ether, tetrahydrofuran and dioxan). Compounds of formula I may be isolated from the separated organic phase in the customary manner, for example by washing and drying the organic phase, distilling off the used solvent and if necessary purifying the resulting product by distillation. The carboxylic esters of formula I are obtained in almost theoretical yield with an enantiomeric purity of more than 99%.

Process Step c)

2(R)-Alkyl-5-halogenpent-4-ene carboxylic acids may be isolated from aqueous-alkaline medium in a manner known per se, for example by precipitating the acid or salts in a suitable medium, or preferably by extraction of the carboxylic acids. To this end, the basic reaction residue is first acidified, for example with mineral acids such as sulfuric acid or hydrochloric acid. An inert organic solvent or solvent mixture is then added which dissolves the acid and is not miscible with water and can therefore be readily separated by the formation of a two-phase system. Suitable solvents are polar organic solvents, in particular ether. After extraction, the organic phases can be washed and dried. The solvent is then removed, for example by distillation, if necessary in a vacuum. The residue remaining after removal of the solvent can be used without further purification in in the next step d). 2(R)-Alkyl-5-halogenpent-4-ene carboxylic acids are obtained in an almost quantitative yield.

Process Step d)

Esterification methods for carboxylic acids are generally known. For example, the esterification may be carried out with alcohols in the presence of mineral acids such as hydrochloric acid or sulfuric acid, the addition of water-binding agents or azeotropic removal of the reaction water being advantageous. It is more expedient to use esterification agents such as diazoalkanes, dialkyl sulfates or acetals, especially activated acetals such as N,N-dimethylaminoformamide dialkyl acetals, which may be used alone or together with appropriate alkali metal alcoholates. The reaction may be performed without or in the presence of inert solvents. The reaction is carried out at an elevated temperature, for example 40 to 150° C., preferably 50 to 100° C.

The carboxylic acids obtained in process step c) may be derivatized before esterification, for example to form acyl halides, in particular chlorides and bromides. Halogenation reagents are known. Inorganic halides such as phosphorus pentachloride or thionyl chloride are frequently used. The acyl halides may be esterified in a manner known per se by reaction with alcohols either without or in the presence of a solvent. The esterification method is exothermic, and cooling of the reaction is advantageous at the start of the reaction. The reaction is then performed at an elevated temperature, for example 40 to 150° C., and preferably 50 to 100° C.

Process Step e)

The (R)-carboxylic ester obtained in process step d) does not need to be isolated for racemization. It is advantageous to perform the racemization in the same reaction vessel following esterification. Methods of racemization are known per se, for example heating to high temperatures and/or adding strong bases. Preferably alkali metal alcoholates are used as bases, especially sodium or potassium alcoholates. When selecting the alcohol for the alcoholate, it is expedient to ensure that it corresponds to the alcohol in the ester group of the (R)-carboxylic ester. If a (R)-carboxylic acid methyl ester is prepared, it is advantageous to use sodium or potassium methylate. The alcoholate may be used in catalytic to equimolar quantities, for example 0.01 to 1 mol, in relation to the (R)-carboxylic ester. If the esterification is carried out with an alkali metal alcoholate via an acyl halide, the quantity of alkali metal alcoholate determined for racemization may already be added during esterification. In this case, racemization may already start to occur during esterification. The reaction temperature may range for example from 40 to 150° C. and preferably from 50 to 100° C. Under the specified conditions, complete racemization is achieved.

The process for isolation of the racemic carboxylic ester may be carried out in a manner known per se. It is advantageous to use extraction methods, as described earlier. The carboxylic esters are obtained in yields of 97% or more, the (R)-carboxylic acid of process step c) being quantitatively converted to the corresponding racemic carboxylic ester. Racemization and esterification are performed consecutively in the same reaction vessel, which offers process engineering advantages.

Process Step f)

The residue obtained after removal of the solvent may be immediately reused as crude product in process step a). Using the process according to the invention, the desired (S)-carboxylic esters can be prepared with very high yields and a high degree of chemical and optical purity, and the undesired (R)-carboxylic acid which inevitably occurs in the separation process can be converted to the desired (S)-carboxylic esters. Complete utilization of the synthesized racemic 2-alkyl-5-halogenpent-4-ene carboxylic ester is thereby achieved, and disposal of the undesired waste product of synthesis, (R)-2-alkyl-5-halogenpent-4-ene carboxylic acid, can be completely avoided.

The following examples explain the invention in more detail.

A) Synthesis of racemic 2-alkyl-5-halogenpent-4-ene carboxylic esters

EXAMPLE A1

Synthesis of

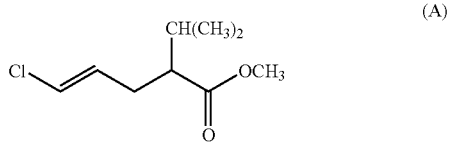

(A)

An agitated solution of 271.3 ml diisopropylamine and 1.6 l tert-butyl methyl ether is cooled to −10° C., and 768 ml 2.5 M n-hexyl lithium solution (in hexane) is added over a period of 15 minutes. The solution is stirred for 5 minutes at −10° C., and then 211.2 ml methyl isovalerate is added drop by drop over a period of 10 minutes. The solution is stirred for 15 minutes, and then 179.6 g potassium tert-butylate in 260 ml 1,2-dimethoxyethane is added over a period of 15 minutes at −10° C. The reaction mixture is stirred for 1 h at −5° C., and then 195.3 g trans-1,3-dichloropropene is added drop by drop. The reaction mixture is stirred for a further 3 hours at −5° C., and then 600 ml aqueous 10 N HCl is added at 0° C. The organic phase is separated off and the aqueous phase extracted with tert-butyl methyl ether (2×0.5 l). The organic phases are washed consecutively with 1N HCl (0.5 l) and aqueous NaCl solution, dried with sodium sulfate and concentrated by evaporation. By means of distillation, title compound A is obtained from the residue as a colourless oil (249.1 g, 79%). $^1$H-NMR (300 MHz, CDCl$_3$, δ): 0.95 (m, 6H), 1.90 (m, 1H), 2.10–2.20 (m, 3H), 3.35 (s, 3H), 5.80–6.0 (m, 2H) ppm.

B) Preparation of (S)-2-alkyl-5-halogenpent-4-ene carboxylic esters

EXAMPLE B1

Preparation of

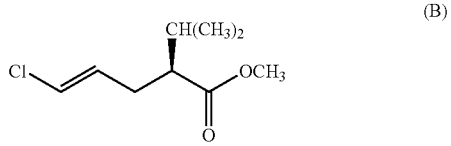

(B)

A solution of 225 g A in 94 ml isopropanol is added to 2.35 l phosphate buffer (pH 7.0). In the presence of 9.42 ml (20700 U) pig liver esterase (Technical Grade, Roche Diagnostics), the mixture is agitated at pH 8.0 and 40° C. until consumption of 623 ml 1.0 N NaOH. The reaction mixture is mixed with tert-butyl methyl ether at room temperature and filtered via Hyflo®. The organic phase is separated off and the aqueous phase extracted with tert-butyl methyl ether (2×1 l). The organic phases are washed consecutively with 5% aqueous Na$_2$CO$_3$ solution (3×0.7 l) and concentrated saline (1×1 l), dried with 300 g Na$_2$SO$_4$, concentrated by evaporation and dried in a vacuum. By means of distillation, title compound B is obtained from the residue as a colourless oil (107.7 g, 47%) with an ee greater than 99%. $^1$H-NMR (300 MHz, CDCl$_3$, δ): 0.95 (m, 6H), 1.90 (m, 1H), 2.10–2.20 (m, 3H), 3.35 (s, 3H), 5.80–6.0 (m, 2H) ppm.

C) Isolation of (R)-2-alkyl-5-halogenpent-4-ene carboxylic acids

EXAMPLE C1

Preparation of

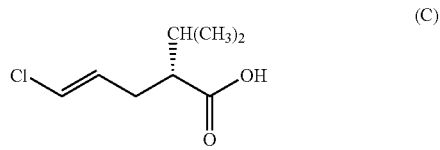

(C)

The alkaline aqueous phases obtained and combined as described under example B1 are acidified at 0° C. with 4N HCl (1 l) and extracted with tert. butyl methyl ether (3×0.7 l). The organic phases are washed with water (0.5 l) and aqueous NaCl solution, dried over sodium sulfate and concentrated on a rotary evaporator. The residue (126 g) corresponds to title compound C, which is used as crude product in examples D1 and D2.

D) Racemization to 2-alkyl-5-halogenpent-4-ene carboxylic esters

Example D1

Preparation of A, esterification with N,N-dimethylformamide dimethyl acetal 106 g C (crude) is heated while stirring to 70° C. 136 ml N,N-Dimethylformamide dimethyl acetal is added drop by drop over a period of 30 minutes at 65–70° C. and stirred under reflux for a further 2 hours. 55.6 ml sodium methylate (5.4 M in methanol) is added drop by drop over a period of 5 minutes at reflux temperature and stirred under reflux for a further 2 hours. The reaction solution is cooled to room temperature, poured onto 1 l water and extracted with tert-butyl methyl ether (2×0.5 l). The organic phases are washed with water/aqueous NaCl solution (9:1; 1 l), dried over sodium sulfate and concentrated on a rotary evaporator.

The residue 110.7 g (97%) corresponds to compound A. Complete racemization is demonstrated by gas chromatography (Lipodex® E, Macherey-Nagel).

EXAMPLE D2

Preparation of A Via Acyl Chloride 106 g C (crude) is heated while stirring to 60° C. 87.3 ml thionyl chloride is added drop by drop over a period of 30 minutes at 60–70° C. (gas evolution) and stirred for a further 60 minutes at 70° C. The thionyl chloride excess is distilled off under a slight vacuum (300–30 mbar) and the residue obtained is cooled to 0° C. 60 ml methanol is then added drop by drop at 0 to not more than 8° C. over a period of 10 minutes. 222 ml sodium methylate (5.4 M in methanol) is added drop by drop at 8–12° C. (exothermic reaction) over a period of 20 minutes. The reaction mixture is heated to reflux and agitated for a further 7 hours. The reaction solution is cooled to room temperature, poured onto ice water (1 l) and extracted with tert-butyl methyl ether (2×0.5 l). The organic phases are washed with water/aqueous NaCl solution (9:1; 1 l), dried over sodium sulfate and concentrated on a rotary evaporator. The residue 111.2 g (97%) corresponds to title compound A. Complete racemization is demonstrated by gas chromatography (Lipodex® E, Macherey-Nagel).

E) Recycling of Compounds A

EXAMPLE E1:

The compound A prepared according to example D1 is subjected to racemate resolution with 115 g fresh compound A as described in example B1. The same separation result is obtained. The recycling as described in examples C1 and D1 may then be continued.

EXAMPLE E2:

The compound A prepared according to example D2 is subjected to racemate resolution with 114 g fresh compound A as described in example B1. The same separation result is obtained. The recycling as described in examples C1 and D2 may then be continued.

What is claimed is:

1. A process for the preparation of 2(S)-alkyl-5-halogenpent-4-ene carboxylic esters by enzymatic hydrolysis, comprising the steps
    a) enzymatic hydrolysis of racemic 2-alkyl-5-halogenpent-4-ene carboxylic esters in aqueous and alkaline medium in the presence of an esterase;
    b) isolation of 2(S)-alkyl-5-halogenpent-4-ene carboxylic esters by extraction with an organic solvent;
    c) isolation of 2(R)-alkyl-5-halogenpent-4-ene carboxylic acids from the aqueous-alkaline medium;
    d) esterification of 2(R)-alkyl-5-halogenpent-4-ene carboxylic acids to 2(R)-alkyl-5-halogenpent-4-ene carboxylic esters,
    e) subsequent racemization to form 2-alkyl-5-halogenpent-4-ene carboxylic esters; and
    f) return of the racemate obtained in step e) to step a), if necessary together with fresh racemic 2-alkyl-5-halogenpent-4-ene carboxylic esters.

2. The process according to claim 1, wherein 2(S)-alkyl-5-halogenpent-4-ene carboxylic ester corresponds to formula I,

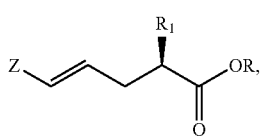

wherein
    R is an organic group with 1 to 18 C-atoms, $R_1$ is $C_1$–$C_6$alkyl, Z is chlorine, bromine or iodine, and the OR group forms an ester group with the carbonyl residue.

3. The process according to claim 1, wherein the racemate used in process a) corresponds to formula II.

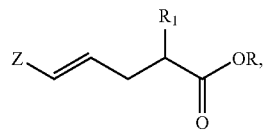

wherein
    R is an organic group with 1 to 18 C-atoms, $R_1$ is $C_1$–$C_6$alkyl, Z is chlorine, bromine or iodine, and the OR group forms an ester group with the carbonyl residue.

4. The process according to claim 1, wherein 2(R)-alkyl-5-halogenpent-4-ene carboxylic acid corresponds to formula III,

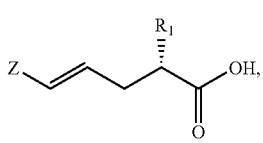

wherein $R_1$ is $C_1$–$C_6$alkyl and Z is chlorine, bromine or iodine.

5. The process according to claim 2, wherein Z is chlorine.

6. The process according to claim 2, wherein R is $C_1$–$C_{18}$alkyl.

7. The process according to claim 6, wherein the alkyl is methyl or ethyl.

8. The process according to claims 2, wherein $R_1$ is $C_1$–$C_4$alkyl, and Z is chlorine.

9. The process according to claims 2, wherein Z is chlorine, $R_1$ is i-propyl, and R is methyl or ethyl.

10. The process according to claim 1, wherein the enzymatic hydrolysis in process step a) is performed with diluted, aqueous KOH or NaOH.

11. The process according to claim 1, wherein the isolation is performed by means of extraction with an organic solvent which is not miscible with water.

12. The process according to claim 1, wherein the 2(R)-alkyl-5-halogenpent-4-ene carboxylic acids are isolated by extraction with an organic solvent, the reaction mixture being acidified beforehand.

13. The process according to claim 1, wherein the 2(R)-alkyl-5-halogenpent-4-ene carboxylic acid is either esterified with an esterification agent, or the carboxylic acid is converted to the acyl halide before esterification.

14. The process according to claim 1, wherein the racemization following the esterification after process step d) is performed in the same reaction vessel without isolation of the 2(R)-alkyl-5-halogenpent-4-ene carboxylic ester.

15. The process according to claim 1, wherein the racemization is performed in the presence of an alkali metal alcoholate at elevated temperatures.

16. The process according to claim 3, wherein Z is chlorine.

17. The process according to claim 4, wherein Z is chlorine.

18. The process according to claim 3, wherein R is $C_1$–$C_{18}$alkyl.

19. The process according to claim 18, wherein the alkyl is methyl or ethyl.

20. The process according to claim 3, wherein $R_1$ is $C_1$–$C_4$alkyl, and Z is chlorine.

21. The process according to claim 4, wherein $R_1$ is $C_1$–$C_4$alkyl, and Z is chlorine.

22. The process according to claim 3, wherein Z is chlorine, $R_1$ is i-propyl, and R is methyl or ethyl.

23. The process according to claim 4, wherein Z is chlorine, $R_1$ is i-propyl, and R is methyl or ethyl.

* * * * *